US00PP12864P2

(12) United States Plant Patent
de Jong

(10) Patent No.: US PP12,864 P2
(45) Date of Patent: Aug. 20, 2002

(54) BOUVARDIA PLANT NAMED 'GREEN SPRING'

(76) Inventor: John M. F. de Jong, Floraweg 67, 2371 AM Roelofarendsveen (NL)

( * ) Notice: Subject to any disclaimer, the term of this patent is extended or adjusted under 35 U.S.C. 154(b) by 0 days.

(21) Appl. No.: 09/419,915

(22) Filed: Oct. 18, 1999

(51) Int. Cl.[7] ..... A01H 5/00
(52) U.S. Cl. ..... Plt./352
(58) Field of Search ..... Plt./352

(56) References Cited

FOREIGN PATENT DOCUMENTS

EP 7011 11/2000

NL BUV 55 3/1997

OTHER PUBLICATIONS

GTITM UPOVROM Citation for 'Green Spring' as per NL PBR BUV0055; Mar. 14, 1997.*

* cited by examiner

*Primary Examiner*—Bruce R. Campell
*Assistant Examiner*—Kent L. Bell
(74) *Attorney, Agent, or Firm*—Foley & Lardner

(57) ABSTRACT

A new and distinct cultivar of Bouvardia plant named 'Green Spring' characterized by having white flowers that are green at the apex, dark-green foliage, short internodes, which makes it suitable for growing as a potplant, and excellent keeping quality.

2 Drawing Sheets

BACKGROUND OF THE INVENTION

The present invention comprises a new and distinct cultivar of Bouvardia plant, botanically known as *Bouvardia salisb*, and hereinafter referred to by the cultivar name 'Green Spring'. Bouvardia is native to Mexico and other countries of Central America. The genus is named after the French medical doctor Charles Bouvard who lived from 1572 to 1657.

The genus Bouvardia is a member of the family Rubiaceae and mainly contains small shrubs. Generally, the flowers of Bouvardia contain a four-lobed calyx and a long tubular, funnel-shaped, corolla with four spreading lobes. There are two carpels and two stigmas and the fruit is a capsule.

Bouvardia plants are generally propagated by soft tip cuttings. For example, mother plants are pruned under temperature conditions whch prevent flower bud formation (20–22° C.). Young shoots with at least two well-developed leaf pairs are rooted.

'Green Spring' is a product of a planned breeding program which had the objective of creating new Bouvardia cultivars having improved quality and flowers of various colors. 'Green Spring' originated from a hybridization made by the inventor in a controlled breeding program in Roelofarendsveen, the Netherlands, in 1996. The female parent was a proprietary Bouvardia selection designated 94.423.34. The male parent was a proprietary Bouvardia selection designated 92.423. 'Green Spring' was discovered and selected as one flowering plant within the progeny of the stated cross by the inventor, John M. F. de Jong, in a controlled environment in Roelofarendsveen, the Netherlands.

The first act of asexual reproduction of 'Green Spring' was accomplished when soft tip cuttings were taken from the originally discovered plant in 1997 in a controlled environment in Roelofarendsveen, the Netherlands by John M. F. de Jong. Horticultural examination of these asexually reproduced plants has demonstrated that the combination of characteristics as herein disclosed for 'Green Spring' are firmly fixed and are retained through successive generations of asexual reproduction.

BRIEF DESCRIPTION OF THE INVENTION

The following traits have been repeatedly observed and are determined to be basic characteristics of 'Green Spring' which, in combination, distinguish this Bouvardia as a new and distinct cultivar:

1. White flowers that are green at the apex;
2. Dark-green foliage;
3. Short internodes, which makes it suitable for growing as a potplant; and
4. Excellent keeping quality.

The following chart illustrates a comparison between Bouvardia 'Green Spring' and the parental cultivars.

| | 'Green Spring' | 94.423.34 | 92.423 |
|---|---|---|---|
| Flower Color | Petalage color: Base of tube is RHS 139D, suffusing into RHS 155D toward the base of petals (both outside and inside). Base of petals RHS 155D (both upper and lower side) suffusing into RHS 139C towards the apex of the petals (both upper and lower side). | The whole flower is white, RHS 155B | Upper side of petals is light pink, RHS 49D. The lower side of petals is white, RHS 155A |
| Leaf Color (Top side) | RHS 139A | RHS 137A | RHS 147A |

'Green Spring' has not been observed under all possible environmental conditions. The phenotype of the new cultivar may vary significantly with variations in environment such as temperature, light intensity, and daylength without any change in genotype. The following observations, measurements, and values describe the pot plants at 12 weeks old, and the plants for the production of cut flowers at 2–4 years old, as grown in Roelofarendsveen, the Netherlands under conditions which approximate those generally used in commercial practice. Unless otherwise stated, the following observations, measurements, and values apply to both pot plants and plants for the production of cut flowers.

BRIEF DESCRIPTION OF THE DRAWING

The accompanying color photographic illustrations show typical flower and foliage characteristics of 'Green Spring', with colors being as true as possible with illustrations of this type.

Sheet 1 is a side view of 'Green Spring'.

Sheet 2 is a top view of the claimed cultivar in bloom showing the flower form.

DETAILED BOTANICAL DESCRIPTION

In the following description, color references are made to The Royal Horticultural Society Colour Chart (R.H.S.).

Origin: Seedling from breeding program.

Parentage:

*Male parent.*—Unnamed plant designated 92.423.

*Female parent.*—Unnamed plant designated 94.423.34.

Classification:

*Botanical.*—A species of the genus *Bouvardia salisb.*

*Commercial.*—Bouvardia cv. 'Green Spring'.

Plant:

*Form.*—A vigorously growing small shrub with oppositely arranged leaves and flowers in terminal cymes.

*Height.*—Average height of pot plants from soil to the top of the inflorescence is 30 cm; the average height from the soil to the leaf plane is 27 cm (depending on growth regulators). Average height of plants for production of cut flowers from the soil to the top of the inflorescence is 140 cm; from the soil to the leaf plane is 134 cm.

*Diameter.*—Average diameter of pot plants is 18 cm; average diameter of plants for the production of cut flowers is 20 cm.

*Growth habit.*—Vigorous: average time to produce a flowering pot plant started with cuttings is 12 weeks; average production cycle of plants for the production of cut flowers is 12 weeks.

*Foliage.*—Quantity: Numerous, 10–15 leaves per stem. Length: 7.5 cm (pot plants); 10 cm (plants for the production of cut flowers). Width: 3.75 cm (pot plants); 5 cm (plants for the production of cut flowers). Shape of leaf: Lanceolate. Apex: Pointed. Base: Narrowed to the petiole. Margin: Smooth, entire. Texture: Smooth. Color: Upper side green RHS 139A; under side green RHS 147B. Petiole Length: 0.3 cm (pot plants); 0.4 cm (plants for the production of cut flowers). Petiole Diameter: 0.15 cm (pot plants); 0.2 cm (plants for the production of cut flowers). Petiole Color: Green RHS 144A.

Bud:

*Form.*—Flask-shaped with flattened tops.

*Color.*—Green RHS 138B.

*Size.*—Small, approximately 1.0 cm in diameter and 2.5–3.0 cm in length.

*Peduncle.*—Length: 0.3 cm (pot plants); 0.4 cm (plants for the production of cut flowers). Width: 0.1 cm. Color: Green RHS 144B. Texture: Smooth. Form: Erect.

Flower:

*Flowering season.*—Continuously year-round.

*Size.*—Diameter: 1.8–2.2 cm. Depth: 2.0–2.5 cm.

*Inflorescence type.*—Compound cymes.

*Inflorescence number.*—Average 2 (pot plants); average 6 (plants for the production of cut flowers).

*Number of flowers per inflorescence.*—Average 25 (pot plants); average 38 (plants for the production of cut flowers).

*Shape.*—Lobed, tubular corolla.

*Petalage.*—Number of Petals: Four. Length: 0.9 cm (pot plants); 1.2 cm (plants for the production of cut flowers). Width: 0.8 cm (pot plants); 1.1 cm (plants for the production of cut flowers). Arrangement: Concentric circle. Form: Elliptical, round. Apex: Pointed. Base: Grown together to the tubular corolla. Margin: Smooth, entire. Texture: Smooth. Appearance: Satiny. Color: Base of both sides of the petals is white (RHS 155D) suffusing into green (RHS 139C) towards the petal apex (both sides); base of the tube is green (RHS 139D) suffusing into white (RHS 155D) towards the base of the petals.

*Sepals.*—Length: Average 0.6 cm (pot plants); average 0.8 cm (plants for production of cut flowers). Width: Average 0.25 cm (pot plants); average 0.3 cm (plants for the production of cut flowers). Number per flower: 4. Shape: Lanceolate. Apex: Pointed. Base: Fused. Margin: Smooth, entire. Color: Upper side green RHS 137A; under side green RHS 138B.

*Persistence.*—Flowers remain on plant eventually becoming dry.

*Main stem or stalk.*—Length: Up to 80.0 cm. Diameter: 0.3 cm (pot plant); 0.4 cm (plants for the production of cut flowers). Color: Green RHS 146C. Aspect: Sturdy and erect. Internode Length: 6.5 cm (pot plants); 9 cm (plants for the production of cut flowers).

*Lasting quality of bloom.*—14–20 days as a cut flower; 35 days as a pot plant.

Reproductive organs:

*Stamens.*—Number: Four. Arrangement: Alternate with petals.

*Anthers.*—Size: Approximately 0.2 cm in length, 0.1 cm in diameter. Color: RHS 1D.

*Filaments.*—Length: Approximately 2.0 cm. Color: White RHS 155D. Pollen: RHS 200D; quantity of pollen grains per anther varies from 2000–5000.

*Pistils.*—Number: One.

*Seeds.*—Number per capsule: Average 18 (pot plants); 23 (plants for the production of cut flowers). Shape: Round. Length: Average 0.18 cm (pot plants); 0.25 cm (plants for the production of cut flowers). Width: Average 0.19 cm (pot plants); 0.25 cm (plants for the production of cut flowers). Color: RHS 202A.

*Fruit.*—Type: Loculicidal capsule, seeds winged. Length: Average 0.5 cm (pot plant); 0.7 cm (plants for the production of cut flowers). Width: Average 0.5 cm (pot plant); 0.7 cm (plants for the production of cut flowers). Diameter: Average 0.5 cm (pot plant); 0.5 cm (plants for the production of cut flowers). Color: RHS 161A.

Other observations:

*Disease/pest resistance/susceptibility.*—Bouvardia 'Green Spring' is susceptible to aphids, white fly, *Fusarium oxysporum, Botryotinia fuckeliana*, Pythium, *Myrothecium roridum.*

*Winter hardiness.*—Bouvardia 'Green Spring' cannot survive temperatures below 0° C.

I claim:

1. A new and distinct cultivar of Bouvardia plant named 'Green Spring', as illustrated and described herein.

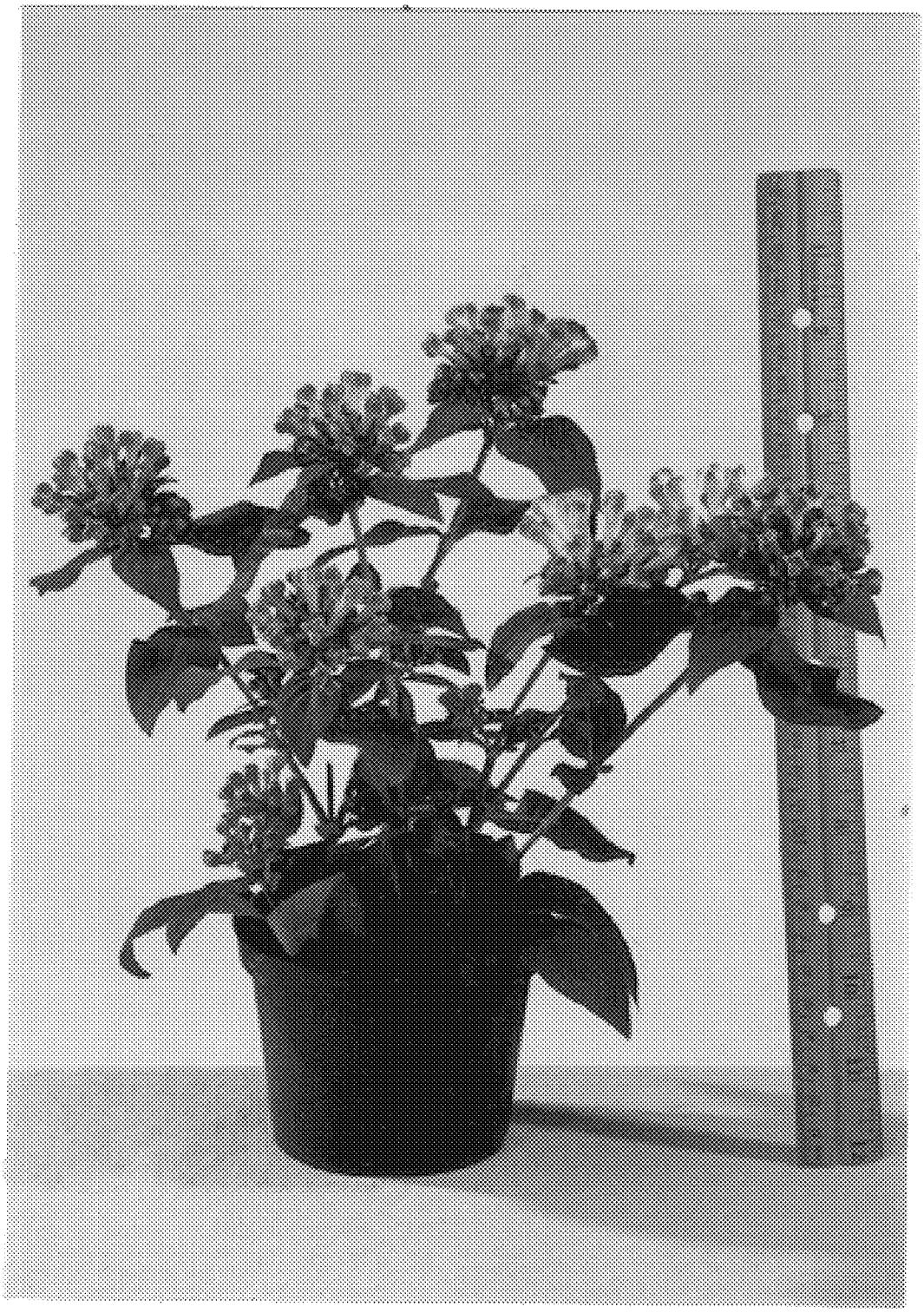

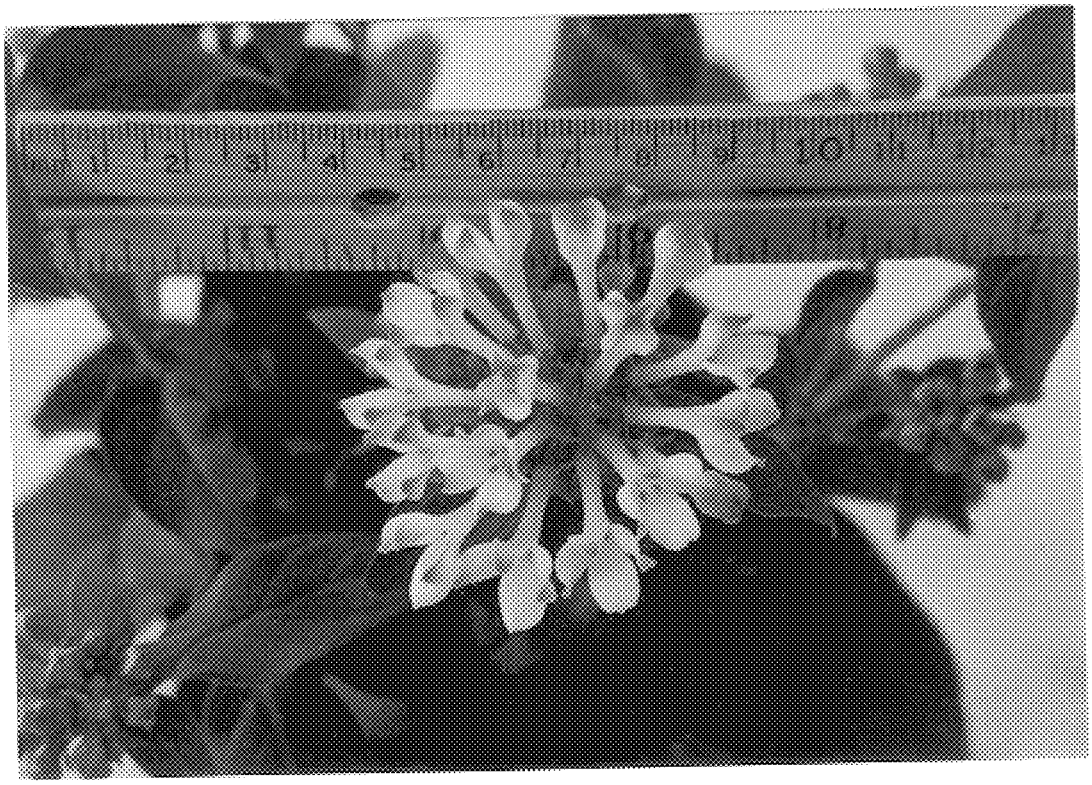

* * * * *